(12) United States Patent
Locke

(10) Patent No.: US 12,194,134 B2
(45) Date of Patent: Jan. 14, 2025

(54) TWO-DOSAGE-FORM ESSENCE AND PREPARATION METHOD THEREOF

(71) Applicant: GUANGZHOU BIOHOPE CO., LTD., Guangzhou (CN)

(72) Inventor: William Locke, Sydney (AU)

(73) Assignee: GUANGZHOU BIOHOPE CO., LTD., Guangzhou (CN)

( * ) Notice: Subject to any disclaimer, the term of this patent is extended or adjusted under 35 U.S.C. 154(b) by 767 days.

(21) Appl. No.: 17/414,595

(22) PCT Filed: Dec. 11, 2019

(86) PCT No.: PCT/CN2019/124636
§ 371 (c)(1),
(2) Date: Jun. 16, 2021

(87) PCT Pub. No.: WO2021/068401
PCT Pub. Date: Apr. 15, 2021

(65) Prior Publication Data
US 2022/0087924 A1    Mar. 24, 2022

(30) Foreign Application Priority Data
Oct. 12, 2019    (CN) .......................... 201910967517.0

(51) Int. Cl.
| | | |
|---|---|---|
| A61K 8/9722 | (2017.01) | |
| A61K 8/04 | (2006.01) | |
| A61K 8/34 | (2006.01) | |
| A61K 8/64 | (2006.01) | |
| A61K 8/92 | (2006.01) | |
| A61Q 19/00 | (2006.01) | |

(52) U.S. Cl.
CPC ............ *A61K 8/9722* (2017.08); *A61K 8/042* (2013.01); *A61K 8/345* (2013.01); *A61K 8/64* (2013.01); *A61K 8/922* (2013.01); *A61Q 19/007* (2013.01)

(58) Field of Classification Search
None
See application file for complete search history.

(56) References Cited

FOREIGN PATENT DOCUMENTS

| | | | |
|---|---|---|---|
| CN | 104940121 A | 9/2015 | |
| CN | 107184429 A | 9/2017 | |
| CN | 107184541 A | 9/2017 | |
| CN | 107252400 A | 10/2017 | |
| CN | 108113904 A | 6/2018 | |
| KR | 2149851 B1 * | 8/2020 | ............... A61K 8/64 |
| RU | 2384326 C2 * | 3/2010 | ........... A61C 19/066 |
| WO | WO-2009016362 A2 | 2/2009 | |

OTHER PUBLICATIONS

RU-2384326-C2 translated doc (Year: 2010).*
KR-2149851-B1 translated doc (Year: 2018).*

* cited by examiner

*Primary Examiner* — Terry A McKelvey
*Assistant Examiner* — Jacob A Boeckelman
(74) *Attorney, Agent, or Firm* — MUNCY, GEISSLER, OLDS & LOWE, P.C.

(57) ABSTRACT

Disclosed is a two-dosage-form essence including oil gel and hydrogel. The oil gel and the hydrogel are mixed according to a preset ratio during use. The oil gel includes the following components in parts by weight: 0.1-6 parts of active ingredient; 15-35 parts of polyol; 0.1-1 part of SODIUM SURFACTIN; 10-70 parts of oil; and 1-10 parts of water. The two-dosage-form essence according to the present application is mixed according to a preset ratio during use, and the oil gel and the hydrogel have a transparent appearance and good stability. Also disclosed is a method for preparing a two-dosage-form essence. The oil gel and the hydrogel are prepared separately. The oil gel is prepared by a D-phase emulsification method. A low amount of emulsifier can emulsify an oil phase with a high oil content.

5 Claims, 8 Drawing Sheets

2

TWO-DOSAGE-FORM ESSENCE AND PREPARATION METHOD THEREOF

TECHNICAL FIELD

The present application relates to the technical field of skin care products, and in particular to a two-dosage-form essence and a preparation method thereof.

BACKGROUND

Currently, many different types of two-dosage-form essences exist on the market, including water and powder combination, white emulsion and transparent gelatin combination, semi-permeable gel and transparent gelatin combination, and the like. For example, Clarins' Double Serum on the market is a two-dosage-form type of oil and water, which is packed in a large tube and a small tube and squeezed out by one pump head. Guerlain's ABEILLE ROYALE is a semi-permeable gelatin and lotion combination with particles, in which the semi-permeable gelatin and the lotion are packed in 2 tubes separately and squeezed out through 1 pump head. Clinique's dark spot corrector & optimizer is a combination of lotion and gelatin, in which the lotion and the gelatin are packed in 2 tubes separately, and when in use, squeezed out through two pump heads separately, and then mixed on the hand. Clinique's dramatically different moisturizing lotion+ is a combination of white emulsion and transparent gelatin, in which the emulsion and the transparent gelatin are packed in a large tube and a small tube sleeved together and squeezed out through one pump head.

That is to say, the main combinations of the two-dosage-form essences on the market are a combination of emulsion and transparent gelatin and a combination of emulsion and semi-permeable gelatin, which can provide a certain degree of moisture to the skin, so that the skin will not be too refreshed. Moreover, the active substances in the two-dosage-form essence can be separated, so that mixing before use will not affect its stability.

However, the existing products on the market are basically a simple blend of two-dosage-form essences. Although there are new ideas in the packaging, with two tubes for separate packing and separate discharge and also with in-tube mixing, the mixing of the basic materials have no significant difference, which is basically a transparent water-based gel with a semi-permeable to milky white oil-in-water essence. It is difficult to make the oil gel transparent, stable and good in skin feel, which has certain requirements for the selection of emulsifiers, the selection and matching of oil, and the selection of polyol.

SUMMARY

In order to overcome the shortcomings of the prior art, a first object of the present application is to provide a two-dosage-form essence composed of oil gel and hydrogel which are mixed in a preset ratio during use and are both transparent and stable.

A second object of the present application is to provide a method for preparing a two-dosage-form essence, in which oil gel and the hydrogel are prepared separately. The oil gel is prepared by a D-phase emulsification method. A low amount of emulsifier can emulsify an oil phase with a high oil content.

The first object of the present application is achieved by adopting the following technical solutions.

A two-dosage-form essence, including oil gel and hydrogel, wherein the oil gel and the hydrogel are mixed according to a preset ratio during use; and the oil gel includes the following components in parts by weight: 0.1-6 parts of active ingredient; 15-35 parts of polyol; 0.1-1 part of SODIUM SURFACTIN; 10-70 parts of oil; and 1-10 parts of water.

Further, the active ingredient includes 0.1-0.5 part of *Laminaria ochroleuca* extract complex, 0.1-0.5 part of algae extract complex, 2-5 parts of complex amino acid, 0.1-1 part of eye circumference mixture; the polyol is one or any combination of glycerin, propylene glycol, 1,3-butylene glycol, sorbitol, and glycereth-26; and the oil is any combination of *Prunus amygdalus dulcis* (SWEET ALMOND) OIL, Canola oil, C15-19 alkanes, *Simmondsia chinensis* (JOJOBA) SEED OIL, sunflower seed oil, soybean oil, squalane, octyldodecanol, mineral oil, dimethylsiloxane and cyclomethicone.

Further, the *Laminaria ochroleuca* extract complex is a composition of caprylic/capric triglyceride and *Laminaria ochroleuca* extract; the algae extract complex is a composition of caprylic/capric triglyceride and algae extract; the complex amino acid is a composition of water, butylene glycol, lysine, histidine, arginine, aspartic acid, threonine, serine, glutamic acid, proline, glycine, alanine, valine, isoleucine, leucine, tyrosine and phenylalanine; the eye circumference mixture is a composition of *Capsicum frutescens* fruit extract, *Citrus grandis* (GRAPEFRUIT) FRUIT EXTRACT, *Ruscus aculeatus* root extract, *Equisetum arvense* extract, *Glycyrrhiza glabra* (LICORICE) ROOT EXTRACT/ascorbyl methylsilanol pectinate, methylsilanol hydroxyproline aspartate, dimethylsilanol hyaluronate, aminoethylphosphinic acid, propylene glycol, butylene glycol, methylpropanediol, ethanol, water, PEG-35 castor oil, phenoxyethanol and sodium benzoate.

Further, the oil gel includes the following components in parts by weight: 2-4 parts of active ingredient; 20-30 parts of polyol; 0.1-1 part of SODIUM SURFACTIN; 40-65 parts of oil; 1-10 parts of water; and 0.001-1 part of pigment.

Further, the oil gel is prepared by a D-phase emulsification method.

Further, the hydrogel includes the following components in parts by weight: 70-90 parts of solvent, 1-15 parts of active component, 0.1-2 parts of thickener, 3-20 parts of humectant, 0-1 part of neutralizer, 0.1-1 part of preservative, 0.001-0.3 part of FRAGRANCE, 0.01-1 part of solubilizer, 0-1 part of pH value regulator, and 0-0.5 part of chelating agent, wherein the active component is an anti-allergic active, a whitening active, an anti-glycation active or an anti-photoactive active.

Further, the hydrogel includes the following components in parts by weight: 70-90 parts of water, 3-8 parts of butylene glycol, 3-10 parts of refined peptide complex, 1-5 parts of phytosterols complex, 1-5 parts of glycereth-26, 0.1-1 part of polyacrylate crosspolymer-6, 0.1-0.5 part of xanthan gum, 0.1-1 part of preservative complex, 0.01-0.2 part of PEG-40 hydrogenated castor oil, and 0.01-0.2 part of FRAGRANCE, wherein the refined peptide complex is a composition of water, polysorbate 20, carbomer, palmitoyl tetrapeptide-7, palmitoyl pentapeptide-4, acetyl hexapeptide-8, glycerol and 1,2-hexanediol; the phytosterols complex is a composition of water, propylene glycol and phytosterols; and the preservative complex is a combination of phenoxyethanol, methylparaben, ethylparaben and ethylhexylglycerin;

or, the hydrogel includes the following components in parts by weight: 1-5 parts of glycereth-26, 1-8 parts of butylene glycol, 80-90 parts of water, 0.1-1 part of polyacrylate crosspolymer-6, 0.05-0.5 part of acrylates/C10-30 alkly acrylate crosspolymer, 0.05-0.5 part of triethanolamine, 0.1-0.5 part of madecassoside, 0.5-2 parts of water/glycerin/*Poncirus trifoliata* fruit extract, 3-8 parts of *Tremella fuciformis*(MUSHROOM) EXTRACT/dipropylene glycol/disodium EDTA/water, 0.5-2 parts of water/butylene glycol/phenoxyethanol/*Ulmus davidiana* root extract, 0.3-1 part of phenoxyethanol/methylparaben/ethylparaben/ethylhexylglycerin, 0.001-0.01 part of FRAGRANCE, and 0.01-0.1 part of PEG-40 hydrogenated castor oil;

or, the hydrogel includes the following components in parts by weight: 80-90 parts of water, 2-5 parts of glycereth-26, 0.1-0.5 part of polyacrylate crosspolymer-6, 0.1-0.5 part of acrylates/C10-30 alkly acrylate crosspolymer, 1-5 parts of niacinamide, 0.1-0.5 part of triethanolamine, 0.01-0.1 part of sodium hyaluronate, 0.5-2 parts of water/butylene glycol/*Magnolia sieboldii* extract, 0.5-2 parts of undecylenoyl phenylalanine, 0.1-1 part of triethanolamine, of 2-5 parts butylene glycol, 0.3-1 part of phenoxyethanol/methylparaben/ethylparaben/ethylhexylglycerin, 0.01-0.1 part of FRAGRANCE, and 0.1-0.3 part of PEG-40 hydrogenated castor oil;

or, the hydrogel includes the following components in parts by weight: 85-95 parts of water, 0.1-0.3 part of xanthan gum, 2-5 parts of glycereth-26, 0.1-0.3 part of carbomer, 0.5-2 parts of decarboxy carnosine HCl/butylene glycol/sodium methylparaben/water, 0.5-2 parts of carnosine, 0.3-1 part of citric acid, 0.3-1 part of *Trigonella foenum-graecum* seed extract, 0.3-1 part of phenoxyethanol/methylparaben/ethylparaben/ethylhexylglycerin, 2-5 parts of butylene glycol, 0.1-0.3 part of PEG-40 hydrogenated castor oil, and 0.01-0.1 part of FRAGRANCE;

or, the hydrogel includes the following components in parts by weight: 75-80 parts of water, 0.1-0.3 part of carbomer, 0.01-0.2 part of xanthan gum, 1-5 parts of water/polysorbate 20/glycerin/1,2-hexanediol/carbomer/palmitoyl tetrapeptide-7, 0.1-1 part of glucosylrutin, 0.1-0.3 part of triethanolamine, 0.01-0.2 part of DISODIUM EDTA, 0.1-1 part of water/propylene glycol/*Buddleja officinalis* extract, 3-5 parts of *Tremella fuciformis* (MUSHROOM) EXTRACT/dipropylene glycol/disodium EDTA/water, 0.3-1 part of phenoxyethanol/methylparaben/ethylparaben/ethylhexylglycerin, 5-10 parts of propylene glycol, 3-8 parts of butylene glycol, 0.01-0.2 part of FRAGRANCE, and 0.1-0.5 part of PEG-40 hydrogenated castor oil.

The second object of the present application is achieved by adopting the following technical solutions.

A method for preparing a two-dosage-form essence, including steps of preparing oil gel and steps of preparing hydrogel, wherein the steps of preparing the oil gel includes:

1) dispersing a formula amount of SODIUM SURFACTIN in a formula amount of polyol, and stirring evenly to obtain an alcohol phase;
2) mixing a formula amount of oil evenly to obtain an oil phase;
3) adding the oil phase dropwise to the alcohol phase, and stirring evenly to obtain a semi-finished product; and
4) adding a formula amount of water and a formula amount of active ingredient to the semi-finished product, and stirring evenly to obtain the oil gel.

Further, the steps of preparing the oil gel includes:

1) dispersing the formula amount of SODIUM SURFACTIN in the formula amount of polyol, and stirring at a speed lower than 600 rpm/min for 5-10 min evenly to obtain the alcohol phase;
2) mixing the formula amount of oil evenly to obtain the oil phase;
3) adding the oil phase dropwise to the alcohol phase, with a dropping rate of 5-10 g/min and a stirring speed of 500-800 rpm/min, to obtain the semi-finished product; and
4) adding the formula amount of water and the formula amount of active ingredient to the semi-finished product, homogenizing for 2-3 minutes, and stirring evenly to obtain the oil gel.

Further, the hydrogel includes the following components in parts by weight: 70-90 parts of water, 3-8 parts of butylene glycol, 3-10 parts of refined peptide complex, 1-5 parts of phytosterols complex, 1-5 parts of glycereth-26, 0.1-1 part of polyacrylate crosspolymer-6, 0.1-0.5 part of xanthan gum, 0.1-1 part of preservative complex, 0.01-0.2 part of PEG-40 hydrogenated castor oil, and 0.01-0.2 part of FRAGRANCE; and the preparation method includes:

mixing a formula amount of xanthan gum, polyacrylate crosspolymer-6 and water evenly, heating to 80° C. for 10-30 minutes, and then adding a formula amount of refined peptide complex, phytosterols complex and glycereth-26 when the temperature is lowered to 45° C. to obtain a first mixture; then dispersing a formula amount of preservative complex evenly with a formula amount of butylene glycol to obtain a second mixture; dispersing a formula amount of FRAGRANCE evenly with a formula amount of PEG-40 hydrogenated castor oil to obtain a third mixture; and finally, adding the second mixture and the third mixture to the first mixture in sequence, and mixing evenly to obtain the hydrogel;

or, the hydrogel includes the following components in parts by weight: 1-5 parts of glycereth-26, 1-8 parts of butylene glycol, 80-90 parts of water, 0.1-1 part of polyacrylate crosspolymer-6, 0.05-0.5 part of acrylates/C10-30 alkly acrylate crosspolymer, 0.05-0.5 part of triethanolamine, 0.1-0.5 part of madecassoside, 0.5-2 parts of water/glycerin/*Poncirus trifoliata* fruit extract, 3-8 parts of *Tremella fuciformis*(MUSHROOM) EXTRACT/dipropylene glycol/disodium EDTA/water, 0.5-2 parts of water/butylene glycol/phenoxyethanol/*Ulmus davidiana* root extract, 0.3-1 of part phenoxyethanol/methylparaben/ethylparaben/ethylhexylglycerin, 0.001-0.01 part of FRAGRANCE, and 0.01-0.1 part of PEG-40 hydrogenated castor oil;

the preparation method includes:

heating, stirring and dispersing evenly a formula amount of glycereth-26, butylene glycol, water, polyacrylate crosspolymer-6, acrylates/C10-30 alkly acrylate crosspolymer; after cooling, adding a formula amount of triethanolamine, madecassoside, water/glycerin/*Poncirus trifoliata* fruit extract, *Tremella fuciformis*(MUSHROOM) EXTRACT/dipropylene glycol/disodium EDTA/water, water/butylene glycol/phenoxyethanol/*Ulmus davidiana* root extract, phenoxyethanol/methylparaben/ethylparaben/ethylhexylglycerin, FRAGRANCE and PEG-40 hydrogenated castor oil, and stirring evenly to obtain the hydrogel;

or, the hydrogel includes the following components in parts by weight: 80-90 parts of water, 2-5 parts of glycereth-26, 0.1-0.5 part of polyacrylate crosspolymer-6, 0.1-0.5 part of acrylates/C10-30 alkly acrylate crosspolymer, 1-5 parts of niacinamide, 0.1-0.5 part of triethanolamine, 0.01-0.1 part of sodium hyaluronate, 0.5-2 parts of water/butylene glycol/*Magnolia sieboldii* extract, 0.5-2 parts of undecylenoyl phenylalanine, 0.1-1 part of triethanolamine, 2-5 parts of butylene glycol, 0.3-1 part of phenoxyethanol/methylparaben/ethylparaben/ethylhexylglycerin, 0.01-0.1 part of FRAGRANCE, and 0.1-0.3 part of PEG-40 hydrogenated castor oil;

the preparation method includes:

dividing a formula amount of water into two parts; heating a first part of water and a formula amount of glycereth-26, polyacrylate crosspolymer-6, acrylates/C10-30 alkly acrylate crosspolymer, and niacinamide and swelling evenly, then adding a formula amount of triethanolamine and stirring to be clear and transparent to obtain a first mixture; then pre-heating a formula amount of undecylenoyl phenylalanine and triethanolamine and a second part of water and stirring to be transparent, and adding a formula amount of sodium hyaluronate, water/butylene glycol/*Magnolia sieboldii* extract to obtain a second mixture, and adding the second mixture to the first mixture, stirring and dispersing evenly to obtain a third mixture; pre-mixing butylene glycol and phenoxyethanol/methylparaben/ethylparaben/ethylhexylglycerin evenly, and mixing the FRAGRANCE and PEG-40 hydrogenated castor oil evenly, and finally adding the same to the third mixture, and stirred evenly to obtain the hydrogel;

or, the hydrogel includes the following components in parts by weight: 85-95 parts of water, 0.1-0.3 part of xanthan gum, 2-5 parts of glycereth-26, 0.1-0.3 part of carbomer, 0.5-2 parts of decarboxy carnosine HCl/butylene glycol/sodium methylparaben/water, 0.5-2 parts of carnosine, 0.3-1 part of citric acid, 0.3-1 part of *Trigonella foenum-graecum* seed extract, 0.3-1 part of phenoxyethanol/methylparaben/ethylparaben/ethylhexylglycerin, 2-5 parts of butylene glycol, 0.1-0.3 part of PEG-40 hydrogenated castor oil, and 0.01-0.1 part of FRAGRANCE;

the preparation method includes:

dividing a formula amount of water into two parts; heating a first part of water and a formula amount of xanthan gum, glycerol-26 and carbomer, stirring evenly, and cooling to 45° C. to obtain a first mixture; mixing *Trigonella foenum-graecum* seed extract and a second part of water, heating to 80° C., dissolving and filtering with filter cloth; taking the filtrate, and adding a formula amount of decarboxy carnosine HCl/butylene glycol/sodium methylparaben/water, carnosine, and citric acid into the first mixed liquid, and stirring evenly to obtain a second mixed liquid; and mixing phenoxyethanol/methylparaben/ethylparaben/ethylhexylglycerin with butylene glycol, and mixing PEG-40 hydrogenated castor oil and FRAGRANCE evenly, adding to the second mixture, stirring evenly to obtain the hydrogel;

or, the hydrogel includes the following components in parts by weight: 75-80 parts of water, 0.1-0.3 part of carbomer, 0.01-0.2 part of xanthan gum, 1-5 parts of water/polysorbate 20/glycerin/1,2-hexanediol/carbomer/palmitoyl tetrapeptide-7, 0.1-1 part of glucosylrutin, 0.1-0.3 part of triethanolamine, 0.01-0.2 part of DISODIUM EDTA, 0.1-1 part of water/propylene glycol/*Buddleja officinalis* extract, 3-5 parts of *Tremella fuciformis*(MUSHROOM) EXTRACT/dipropylene glycol/disodium EDTA/water, 0.3-1 part of phenoxyethanol/methylparaben/ethylparaben/ethylhexylglycerin, 5-10 parts of propylene glycol, 3-8 parts of butylene glycol, 0.01-0.2 part of FRAGRANCE, and 0.1-0.5 part of PEG-40 hydrogenated castor oil;

the preparation method includes:

dispersing a formula amount of water, carbomer, DISODIUM EDTA and xanthan gum evenly, then adding triethanolamine and stirring evenly to be clear and transparent to obtain a first mixture; adding in turn a formula amount of water/polysorbate 20/glycerin/1,2-hexanediol/carbomer/palmitoyl tetrapeptide-7, glucosylrutin, water/propylene glycol/*Buddleja officinalis* extract, *Tremella fuciformis* (MUSHROOM) EXTRACT/dipropylene glycol/disodium EDTA/water, and stirring evenly to obtain a second mixture; and mixing phenoxyethanol/methylparaben/ethylparaben/ethylhexylglycerin and propylene glycol and butylene glycol evenly, mixing PEG-40 hydrogenated castor oil and FRAGRANCE evenly, adding the second mixed liquid, and stirring evenly to obtain the hydrogel.

Compared with the prior art, the present application has the following beneficial effects.

(1) The two-dosage-form essence according to the present application is composed of two transparent essences, oil gel and hydrogel, which have excellent stability. The two transparent gels are mixed in a certain ratio and subjected to secondary emulsification to obtain various milky white emulsions with different skin feels. SODIUM SURFACTIN is used as an emulsifier of the oil gel, which comes from natural sources and is fermented by *Bacillus subtilis*. It is mild to the skin, has anti-inflammatory effects, can improve skin permeability, and has a very high emulsification ability. A dosage as low as 0.1% can emulsify 15% or even higher oil.

(2) The method for preparing a two-dosage-form essence according to the present application adopts a D-phase emulsification method to prepare the oil gel. Compared with the traditional oil-in-water formula, the D-phase emulsification method has the following advantages.

a. Cold preparation is feasible without heating during the entire production process, which can reduce carbon emissions, shorten production time, and reduce production costs.

b. The amount of emulsifier is very low. In this system, only 0.1-0.5% of emulsifier is needed, which greatly reduces the amount of emulsifier and reduces the risk of formula irritation.

c. It can emulsify an oil phase with a high oil content. In this system, 40-70% of the oil can be emulsified. In case of an ordinary oil-in-water emulsifier, the oil cannot be emulsified at all with such a low amount of emulsifier.

d. The paste has a unique appearance, which can make a very clear and transparent gel, as well as a bright, delicate and translucent paste. The emulsified particle size of the paste is small, and the material diameter distribution is very uniform.

DETAILED DESCRIPTION

The present application will be further described with reference to the accompanying drawings and specific embodiments hereinafter. It should be noted that the embodiments or technical features described hereinafter can be arbitrarily combined to form new embodiments without conflict.

A two-dosage-form essence includes oil gel and hydrogel which are mixed according to a preset ratio during use. The oil gel includes the following components in parts by weight: 0.1-6 parts of active ingredient; 15-35 parts of polyol; 0.1-1 part of SODIUM SURFACTIN; 10-70 parts of oil; and 1-10 parts of water.

Figure 1:
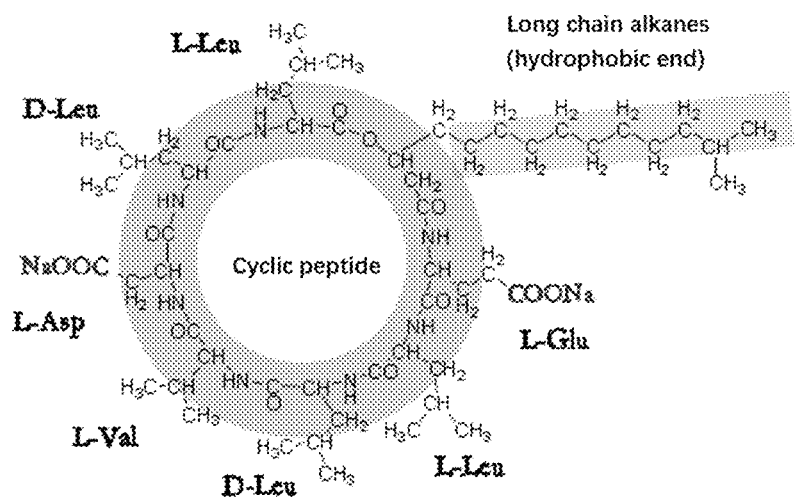
FIG. 1 is a schematic diagram of the structure of SODIUM SURFACTIN.
Figure 2:
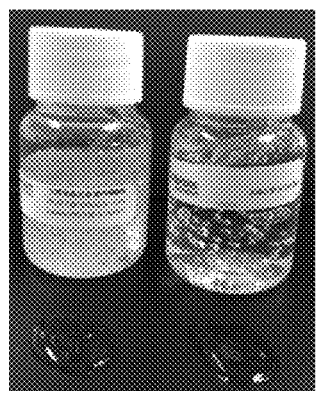
FIG. 2 is an illustration showing oil gel and hydrogel respectively taken out.
Figure 3:
FIG. 3 is an illustration showing the oil gel and the hydrogel just mixed.
Figure 4:
FIG. 4 is another illustration showing the oil gel and the hydrogel just mixed.
Figure 5:
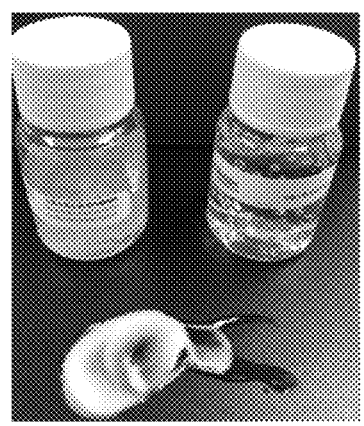
FIG. 5 is an illustration showing the oil gel and the hydrogel mixed evenly completely.
Figure 6:
FIG. 6 is a schematic diagram of the oil gel of Example 1 of the present application.
Figure 7:
FIG. 7 is a schematic diagram of the oil gel of Example 2 of the present application.
Figure 8:
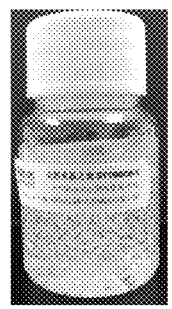
FIG. 8 is a schematic diagram of the oil gel of Example 3 of the present application.
Figure 9:
FIG. 9 is a schematic diagram of the oil gel of Comparative Example 1.
Figure 10:
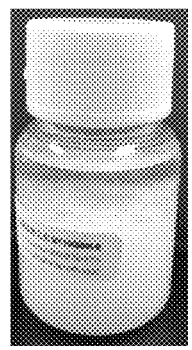
FIG. 10 is a schematic diagram of the oil gel of Comparative Example 2.
Figure 11:
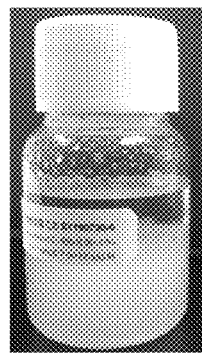
FIG. 11 is a schematic diagram of the oil gel of Comparative Example 3.
Figure 12:
FIG. 12 is a schematic diagram of the oil gel of Comparative Example 4.
Figure 13:
FIG. 13 is a schematic diagram of the oil gel of Comparative Example 5.
Figure 14:
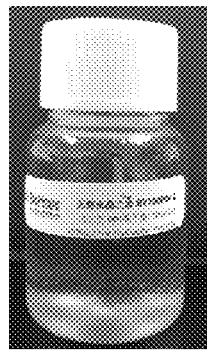
FIG. 14 is a schematic diagram of the oil gel of Comparative Example 6.
Figure 15:
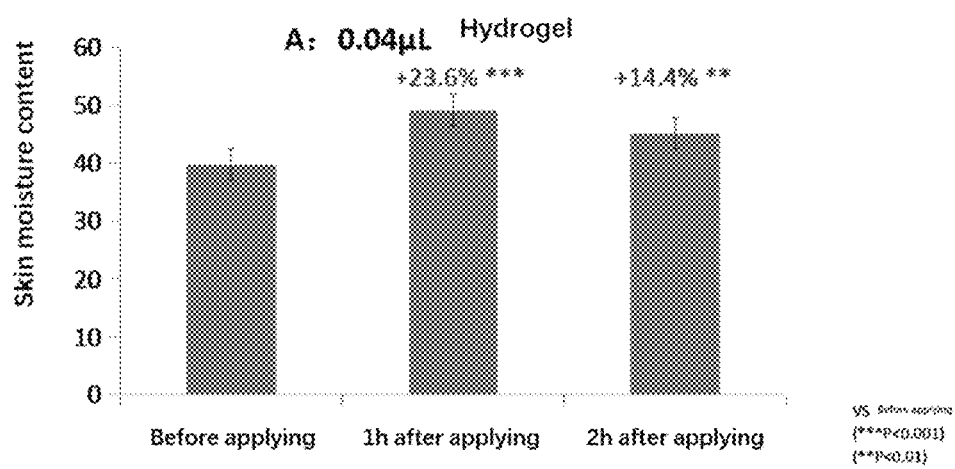
FIG. 15 is a chart showing the moisturizing effect of the hydrogel when used alone.
Figure 16:
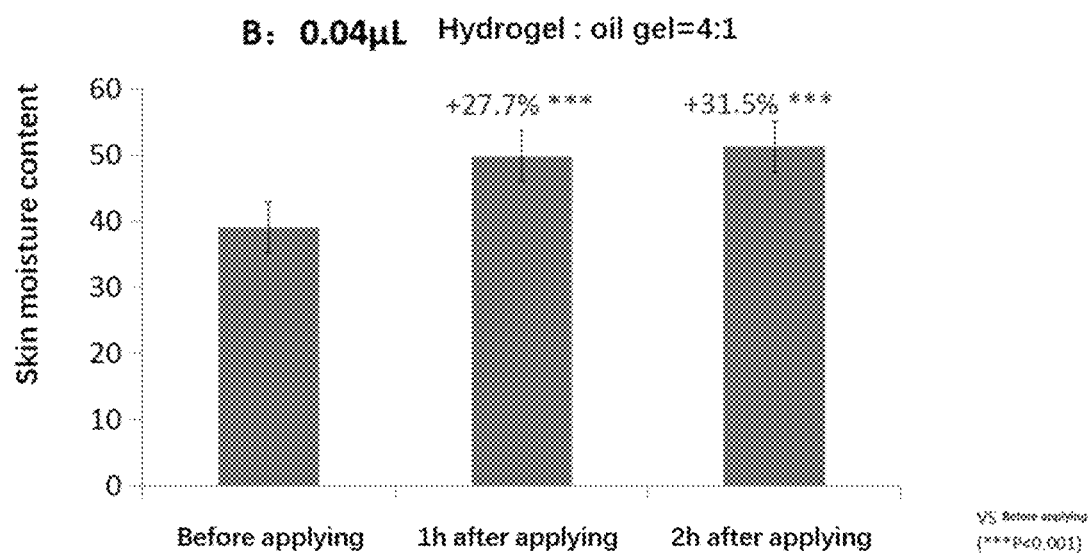
FIG. 16 is a chart showing the moisturizing effect when the hydrogel and the oil gel are mixed in a ratio of 4:1.
Figure 17:
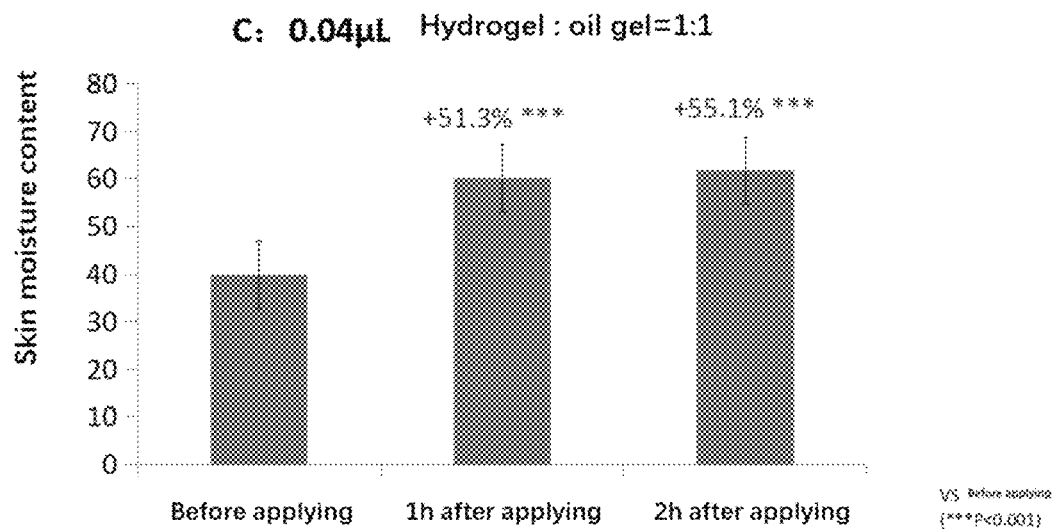
FIG. 17 is a chart showing the moisturizing effect when the hydrogel and the oil gel are mixed in a ratio of 1:1.
Figure 18:
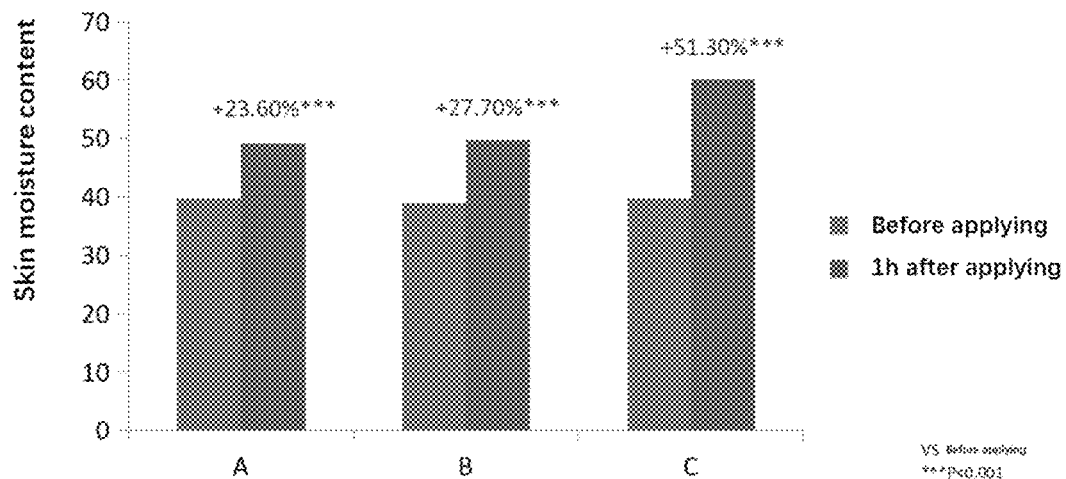
FIG. 18 is a chart showing the moisturizing effect of samples A, B and C before use and 1 hour after use.
Figure 19:
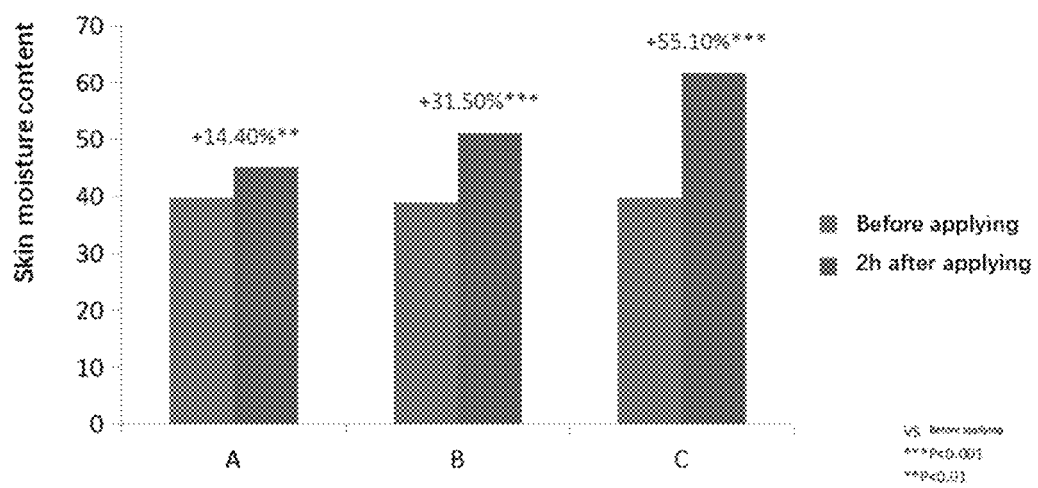
FIG. 19 is a chart showing the moisturizing effect of samples A, B and C before use and 1 hour after use.
Figure 20:
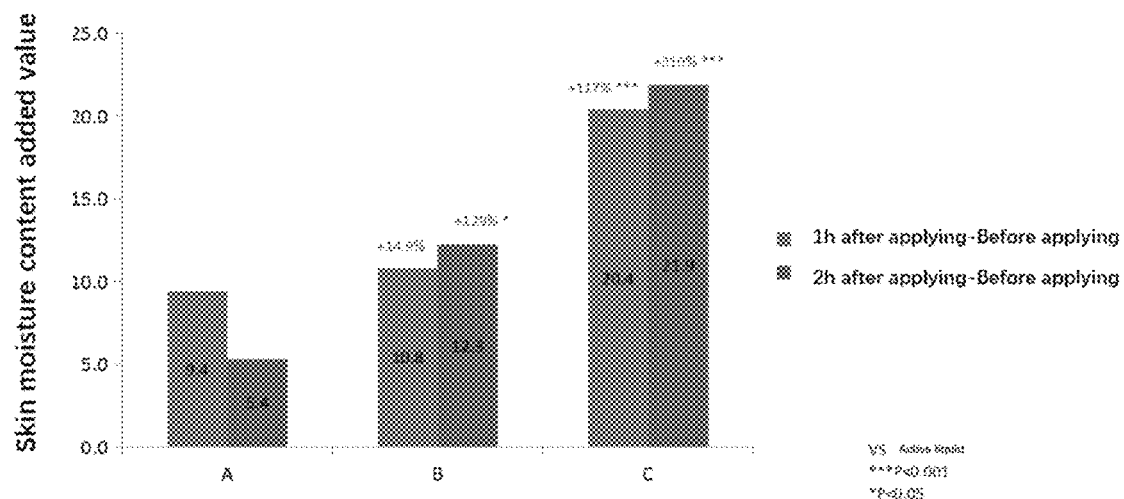
FIG. 20 is a chart showing the moisturizing effect of samples A, B and C 1 hour after use and 2 hours after use.

SODIUM SURFACTIN is selected as an emulsifier, which comes from nature and is fermented by *Bacillus subtilis*. As shown in FIG. 1, it is a circular polypeptide composed of seven amino acids. It is a green and natural polypeptide emulsifier, mild to the skin, has an anti-inflammatory effect, can improve skin permeability and has a very high emulsifying ability. A dosage as low as 0.1% can emulsify 15% or even higher oil.

Water is mainly used to adjust the refractive index of the oil-water phase of the formula.

As a further embodiment, the active ingredient includes 0.1-0.5 part of *Laminaria ochroleuca* extract complex, 0.1-0.5 part of algae extract complex, 2-5 parts of complex amino acid, 0.1-1 part of eye circumference mixture. The *Laminaria ochroleuca* extract complex is a composition of caprylic/capric triglyceride and *Laminaria ochroleuca* extract. The algae extract complex is a composition of caprylic/capric triglyceride and algae extract. The complex amino acid is a composition of water, butylene glycol, lysine, histidine, arginine, aspartic acid, threonine, serine, glutamic acid, proline, glycine, alanine, valine, isoleucine, leucine, tyrosine and phenylalanine. The *Laminaria ochroleuca* extract is derived from the "golden seaweed" living in the harsh marine environment. Under the influence of various factors such as the internal and external salinity changes, seawater immersion/non-immersion changes and changes in the intensity of sunlight, the *Laminaria ochroleuca* has formed a unique survival mechanism. It mainly has active ingredients with comprehensive anti-inflammatory, anti-aging and sun-protection functions.

In addition, the eye circumference mixture is a composition of *Capsicum frutescens* fruit extract, *Citrus grandis* (GRAPEFRUIT) FRUIT EXTRACT, *Ruscus aculeatus* root extract, *Equisetum arvense* extract, *Glycyrrhiza glabra* (LICORICE) ROOT EXTRACT/ascorbyl methylsilanol pectinate, methylsilanol hydroxyproline aspartate, dimethylsilanol hyaluronate, aminoethylphosphinic acid, propylene glycol, butylene glycol, methylpropanediol, ethanol, water, PEG-35 castor oil, phenoxyethanol and sodium benzoate.

As a further embodiment, the polyol is one or any combination of glycerin, propylene glycol, 1,3-butylene glycol, sorbitol, and glycereth-26, and preferably glycerin.

As a further embodiment, all the oil comes from natural sources. The oil is any combination of *Prunus amygdalus dulcis* (SWEET ALMOND) OIL, Canola oil, C15-19 alkanes, *Simmondsia chinensis* (JOJOBA) SEED OIL, sunflower seed oil, soybean oil, squalane, octyldodecanol, mineral oil, dimethylsiloxane and cyclomethicone. The ratio of the oil phase may be 10-70%, particularly preferably 40-65%.

As a further embodiment, the oil gel includes the following components in parts by weight: 2-4 parts of active ingredient; 20-30 parts of polyol; 0.1-1 part of SODIUM SURFACTIN; 40-65 parts of oil; 1-10 parts of water; and 0.001-1 part of pigment.

As a further embodiment, the oil gel is prepared by a D-phase emulsification method. The oil gel is obtained by a D-phase emulsification process. With only 0.1-0.5% dosage of emulsifier, up to 50-70% of the oil can be emulsified, and a clear and transparent oil gel can be prepared. If necessary, an anhydrous formula can also be prepared with an emulsion particle size of 2-10 microns.

As a further embodiment, the oil gel further includes 0.001-1 part of pigment.

As a further embodiment, the hydrogel includes the following components in parts by weight: 70-90 parts of water, 3-8 parts of butylene glycol, 3-10 parts of refined peptide complex, 1-5 parts of phytosterols complex, 1-5 parts of glycereth-26, 0.1-1 part of polyacrylate crosspolymer-6, 0.1-0.5 part of xanthan gum, 0.1-1 part of preservative complex, 0.01-0.2 part of PEG-40 hydrogenated castor oil, and 0.01-0.2 part of FRAGRANCE.

As a further embodiment, the refined peptide complex is a composition of water, polysorbate 20, carbomer, palmitoyl tetrapeptide-7, palmitoyl pentapeptide-4, acetyl hexapeptide-8, glycerol and 1,2-hexanediol. The phytosterols complex is a composition of water, propylene glycol and phytosterols. The preservative complex is a combination of phenoxyethanol, methylparaben, ethylparaben and ethylhexylglycerin.

The two-dosage-form essence according to the present application is composed of two transparent essences. The oil gel formula is basically of a natural origin and does not contain fragrance preservatives. The oil gel is prepared by the D-phase process with natural fermented SODIUM SURFACTIN as the emulsifier and the natural origin oil as the main body. The hydrogel is a transparent water-soluble gel made from a water-soluble polymer. When in use, the two transparent gels are mixed in a certain ratio and subjected to secondary emulsification to obtain milky white emulsions with different skin feels.

The change process during use is shown in FIGS. 2-5.

That is, when in use, the transparent oil gel and the transparent water-based gel (hydrogel) are pumped to the palm of one hand separately and immediately become a milky white emulsion after being mixed by fingers at room temperature to produce a secondary emulsification, which can bring about an instant magic experience to the customer. Due to the high oil phase content of the transparent oil gel, the customer can obtain different types of products by adjusting different dosages of the two transparent gelatins during use. For example, when oil gel:hydrogel is mixed at 1:1, a massage essence can be obtained. When oil gel: hydrogel is mixed at 1:2, moisturizing essence milk can be obtained. When oil gel:hydrogel is mixed in 1:5, it can be used as a body lotion. When oil gel:hydrogel is mixed in 1:20, it can be used as a moisturizer. Therefore, the two-dosage-form essence according to the present application can derive a lot of skin care products, which can greatly streamline the cosmetic bag of the beauty lady during a short business trip or travel, or occasionally use it in emergency.

A method for preparing a two-dosage-form essence includes steps of preparing oil gel and steps of preparing hydrogel.

The steps of preparing the oil gel includes:
1) dispersing a formula amount of SODIUM SURFACTIN in a formula amount of polyol, and stirring evenly to obtain an alcohol phase;
2) mixing a formula amount of oil evenly to obtain an oil phase;
3) adding the oil phase dropwise to the alcohol phase, and stirring evenly to obtain a semi-finished product; and
4) adding a formula amount of water and a formula amount of active ingredient to the semi-finished product, and stirring evenly to obtain the oil gel.

The steps of preparing the hydrogel includes: mixing a formula amount of xanthan gum, polyacrylate crosspolymer-6 and water evenly, heating to 80° C. for 10-30 minutes, and then adding a formula amount of refined peptide complex, phytosterols complex and glycereth-26 when the temperature is lowered to 45° C. to obtain a first mixture; then dispersing a formula amount of preservative complex evenly with a formula amount of butylene glycol to obtain a second mixture; dispersing a formula amount of FRAGRANCE evenly with a formula amount of PEG-40 hydrogenated castor oil to obtain a third mixture; and finally, adding the second mixture and the third mixture to the first mixture in sequence, and mixing evenly to obtain the hydrogel.

As a further embodiment, the steps of preparing the oil gel includes:
1) dispersing the formula amount of SODIUM SURFACTIN in the formula amount of polyol, and stirring at a speed lower than 600 rpm/min for 5-10 min evenly to obtain the alcohol phase;
2) mixing the formula amount of oil evenly to obtain the oil phase;
3) adding the oil phase dropwise to the alcohol phase, which should ensure that the oil phase is added slowly before the gel is formed, with a dropping rate of 5-10 g/min and a stirring speed of 500-800 rpm/min, and stirring to form thick gel to obtain the semi-finished product; and
4) adding the formula amount of water and the formula amount of active ingredient to the semi-finished product, homogenizing for 2-3 minutes, and stirring evenly to obtain the oil gel. Water is used to adjust the transparency of the product.

The method for preparing a two-dosage-form essence according to the present application is obviously different in the operation process. First, the emulsifier SODIUM SURFACTIN should be evenly dispersed with polyol. Then the oil phase is slowly added dropwise to the polyol+emulsifier phase while stirring at medium speed, and the consistency of the paste will increase significantly during the stirring process. Finally, if necessary, the refractive index of the oil-water phase can be adjusted with a small amount of water to obtain a clear and transparent gel.

Compared with the traditional oil-in-water formulation process, the D-phase emulsification process is significantly different in operation process.

First, the emulsifier SODIUM SURFACTIN should be evenly dispersed with glycerin. Then the oil phase is slowly added dropwise to the glycerin+emulsifier phase while stirring at medium speed, and the consistency of the paste will increase significantly during the stirring process. Finally, if necessary, the refractive index of the oil-water phase can be adjusted with a small amount of water to obtain a clear and transparent gel.

Compared with the traditional oil-in-water formula, the advantages of the D-phase emulsification method are as follows.
a. Cold preparation is feasible without heating during the entire production process, which can reduce carbon emissions, shorten production time, and reduce production costs.
b. The amount of emulsifier is very low. In this system, only 0.1-0.5% of emulsifier is needed, which greatly reduces the amount of emulsifier and reduces the risk of formula irritation.
c. It can emulsify an oil phase with a high oil content. In this system, 40-70% of the oil can be emulsified. In case of an ordinary oil-in-water emulsifier, the oil cannot be emulsified at all with such a low amount of emulsifier.
d. The paste has a unique appearance, which can make a very clear and transparent gel, as well as a bright, delicate and translucent paste, and the emulsified particle size of the paste is small, and the material diameter distribution is very uniform.

The following are specific embodiments of the present application. The raw materials, equipment, and the like used in the following embodiments can be obtained through purchase except for special restrictions.

Example 1-7

A two-dosage-form essence includes oil gel and hydrogel. The oil gel and the hydrogel are mixed according to a preset ratio when in use. The oil gel is prepared from the following components: active ingredients, polyols, SODIUM SURFACTIN, oil and water. The hydrogel is prepared from the following components: water, butylene glycol, refined sepin complex (composition of water, polysorbate 20, carbomer, palmitoyl tetrapeptide-7, palmitoyl pentapeptide-4, acetyl hexapeptide-8, glycerol and 1,2-hexanediol), phytosterols complex (composition of water, propylene glycol and phytosterol), glycerol poly Ether-26, polyacrylate crosspolymer-6, xanthan gum, preservative complex (composition of phenoxyethanol, methylparaben, ethylparaben and ethylhexylglycerin), PEG-40 hydrogenated Castor oil, and FRAGRANCE. (The specific formulations of the oil gels of Examples 1-3 are shown in Table 1, and the formulations of the oil gels of Examples 4-7 are consistent with those in Example 1. The specific formulations of the hydrogel of Examples 1-3 are shown in Table 3, and the formulations of the hydrogel of Example 4-7 is shown in Table 4-7. The total amount of components in the same example is 100 parts).

In this application (as in Table 1-7), the raw material connected by "/" means that the raw material is a composite raw material and is a whole.

Comparative Examples 1-6

A two-dosage-form essence includes oil gel and hydrogel. The oil gel and the hydrogel are mixed according to a preset ratio during use. (See Table 1 for the specific formulation of the oil gel, and Table 3 for the specific formulation of the hydrogel. The total amount of components in the same comparative example is 100 parts).

TABLE 1

Formulations of the oil gels of Examples 1-3 and Comparative Examples 1-6

| | Raw material | INCI name | Example 1 | Example 2 | Example 3 | Comparative example 1 | Comparative example 2 | Comparative example 3 | Comparative example 4 | Comparative example 5 | Comparative example 6 |
|---|---|---|---|---|---|---|---|---|---|---|---|
| Polyol | Glyceryl | Glyceryl | 30 | 30 | 30 | 30 | 30 | 30 | 30 | 5 | 30 |
| | Propylene Glycol | Propylene Glycol | 0 | 0 | 0 | 0 | 0 | 0 | 0 | 25 | 0 |
| Emulsifier | KANEKA SF | SODIUM SURFACTIN | 0.3 | 0.3 | 0.5 | 0.3 | 0.1 | 0 | 0.3 | 0.3 | 0.3 |
| | AMPHISOL K | Hexadecanyl Phosphate Potassium Salt | 0 | 0 | 0 | 0 | 0 | 1 | 0 | 0 | 0 |
| Oil | EMOGREEN L15 | C15-19 alkane | 27 | 29 | 27 | 35 | 27 | 27 | 8 | 27 | 27 |
| | DW Jojoba Colorless | SIMMONDSIA CHINENSIS seed oil | 1 | 1 | 1 | 1 | 1 | 1 | 20 | 1 | 1 |
| | Canola Oil | Canola oil/tert-butyl hydroquinone | 18 | 20 | 18 | 9.8 | 18 | 18 | 18 | 18 | 18 |
| | LIPOVOL ALM | PRUNUS AMYGDALUS DULCIS oil | 18 | 14 | 18 | 18 | 18 | 18 | 18 | 18 | 18 |
| Active | ANTILEUKINE 6 | Capylic acid/Capric triglyceride/LAMINARIA OCHROLEUCA extract | 0.3 | 0.3 | 0.3 | 0.3 | 0.3 | 0.3 | 0.3 | 0.3 | 0.3 |
| | JUVENESSENCE AD | Capylic/Capric Triglyceride/Algae Extract | 0.2 | 0.2 | 0.2 | 0.2 | 0.2 | 0.2 | 0.2 | 0.2 | 0.2 |
| | AMINO ACOD COMPLEX | Water/Butylene glycol/Lysine/Histidine/Arginine/Aspartic acid/Threonine/Serine/Glutamic acid/Proline/Glycine/Alanine/Valine/Isoleucine Acid/Leucine/Tyrosine/Phenylalanine | 3 | 3 | 3 | 3 | 3 | 3 | 3 | 3 | 3 |
| | EXSY 509Y324 | CAPSICUM FRUTESCENS fruit extract/CITRUS PARADISI fruit extract/RUSCUS ACULEATUS root extract/EQUISETUM ARVENSE extract/GLYCYRRHIZA GLABRA root extract/Ascorbic acid methylsilanol pectinate/methyl silanol hydroxyproline aspartate/dimethylsilanol hyaluronic acid ester/aminoethyl phosphinic acid/propylene glycol/butylene | 0.5 | 0.5 | 0.5 | 0.5 | 0.5 | 0.5 | 0.5 | 0.5 | 0.5 |

TABLE 1-continued

Formulations of the oil gels of Examples 1-3 and Comparative Examples 1-6

| | Raw material | INCI name | Example 1 | Example 2 | Example 3 | Comparative example 1 | Comparative example 2 | Comparative example 3 | Comparative example 4 | Comparative example 5 | Comparative example 6 |
|---|---|---|---|---|---|---|---|---|---|---|---|
| | Water Pigment | glycol/formaldehyde Propylene glycol/ethanol/water/PEG-35 castor oil/phenoxyethanol/sodium benzoate Water | Margin q.s. | Margin q.s. | Margin q.s. | Margin q.s. | Margin q.s. | Margin q.s. | Margin q.s. | Margin q.s. | Margin q.s. |
| State | | | Paste OK | Paste OK | Paste OK | Slightly cloudy, not transparent enough | Cannot emulsify | Cannot emulsify | cold-resistance, thinning and unstable | Cannot emulsify | Cannot emulsify |
| Difference | | | Optimal ratio | | Increase the amount of emulsifier | Adjust the amount of oil phase | Reduce the amount of emulsifier | Change to other emulsifier | Change the oil with a higher freezing point | Reduce the amount of glyceryl | Change the process, direct oil-water phase homogenization |

The steps of preparing the oil gels of Examples 1-3 and Comparative Examples 1-5 include:

1) dispersing a formula amount of SODIUM SURFACTIN in a formula amount of polyol, and stirring at a speed lower than 600 rpm/min for 5-10 min evenly to obtain an alcohol phase;
2) mixing a formula amount of oil evenly to obtain an oil phase;
3) adding the oil phase dropwise to the alcohol phase, which should ensure that the oil phase is added slowly before the gel is formed, with a dropping rate of 5-10 g/min and a stirring speed of 500-800 rpm/min, and stirring to form thick gel to obtain a semi-finished product; and
4) adding a formula amount of water and a formula amount of active ingredient to the semi-finished product, homogenizing for 2-3 minutes, and stirring evenly to obtain the oil gel.

The preparation process of the oil gel of Comparative Example 6 is changed and the oil gel is directly obtained by homogenizing the oil-water phase.

FIGS. 6-14 are schematic diagrams of the oil gels of Examples 1-3 and Comparative Examples 1-6, and their formulations and differences in properties are shown in Table 2.

TABLE 2

Comparison table of formulations and properties of oil gels of Examples 1-3 and Comparative Examples 1-6

| | Formula difference description | State | Stability |
|---|---|---|---|
| Example 1 | Optimal ratio (best example) | Clear transparent gelatin | Heat and cold resistance OK |
| Example 2 | Adjust the amount of oil | Clear transparent gelatin | Heat and cold resistance OK |
| Example 3 | Increase the amount of emulsifier | Clear transparent gelatin | Heat and cold resistance OK |
| Comparative example 1 | Adjust the amount of oil phase | Slightly cloudy, not transparent enough | Heat and cold resistance OK |
| Comparative example 2 | Reduce the amount of emulsifier | The oil phase is added to the glyceryl phase. After ⅔ of the oil phase is added, it cannot be emulsified, and the consistency will not increase. After the stirring is stopped, the oil will begin to appear. The upper layer is transparent liquid, and the lower layer is milky white. | Unstable at room temperature |
| Comparative example 3 | Change to other emulsifier | The oil phase is added to the glyceryl phase. When 50% of the oil phase is added, it cannot be emulsified. | Unstable at room temperature |
| Comparative example 4 | Change to oil with a higher freezing point | The paste is cloudy and not transparent enough | Cold-resistant, thinning and unstable |
| Comparative example 5 | Reduce the amount of glyceryl and increase the amount of propylene glycol | The oil phase is added to the glyceryl phase. It can thicken at the beginning, and cannot be emulsified when 50% of the oil | Oily at room temperature |

TABLE 2-continued

Comparison table of formulations and properties of oil gels of Examples 1-3 and Comparative Examples 1-6

| | Formula difference description | State | Stability |
|---|---|---|---|
| Comparative example 6 | Change the process, and directly homogenize the oil-water phase | phase is added. The paste is thin, and the oil will appear at room temperature for half an hour It cannot emulsify at all during homogenization, and the oil and water will be separated immediately. | Oily at room temperature |

The hydrogels of Example 1 and Comparative Examples 1-6 are all prepared according to the formula in Table 3. The preparation process includes:

mixing a formula amount of xanthan gum, polyacrylate crosspolymer-6 and water evenly, heating to 80° C. for 10-30 minutes, and then adding a formula amount of refined peptide complex, phytosterols complex and glycereth-26 when the temperature is lowered to 45° C. to obtain a first mixture; then dispersing a formula amount of preservative complex evenly with a formula amount of butylene glycol to obtain a second mixture; dispersing a formula amount of FRAGRANCE evenly with a formula amount of PEG-40 hydrogenated castor oil to obtain a third mixture; and finally, adding the second mixture and the third mixture to the first mixture in sequence, and mixing evenly to obtain the hydrogel.

TABLE 3

Formulations of the hydrogels of Examples 1-3 and Comparative Examples 1-6

| | Raw material | Dosage (by weight) | INCI name | Supplier |
|---|---|---|---|---|
| A | Satiaxane™ VPC 930 | 0.20 | Xanthan gum | Cargill |
| | SEPIMAX ZEN | 0.35 | Polyacrylate crosspolymer-6 | SEPPIC |
| | LIPONIC BIO EG-1 | 2.0 | Glyceryl-26 | Vantage |
| | Water | To100 | Deionized water | |
| B | BPN-tesoro ® 1600 solution Refined peptides | 5.0 | Water/polysorbate-20/carbomer/palmitoyl tetra-peptide-7/palmitoyl pentapeptide-4/acetyl hexapeptide-8/glycerol/1,2-hexanediol | United Laboratories |
| | REVERSKIN | 2.0 | Water/propylene glycol/phytosterols | GREEN-TECH |
| C | 1.3-BG | 5.0 | Butylene glycol | OXEA |
| | EUXYL K350 | 0.6 | Phenoxyethanol/Methylparaben/Ethylparaben/Ethylhexyl glyceryl | S&M |
| D | TAGAT CH40 | 0.05 | PEG-40 hydrogenated castor oil | EVONIK |
| | Flavor 86424049 | 0.02 | Flavor | DROM |

TABLE 4

Formulation of the hydrogel of Example 4

| | Raw material | Dosage % | INCI Name | Supplier |
|---|---|---|---|---|
| A | Liponic ® BIO EG-1 | 2.0 | Glyceryl-26 | VANTAGE |
| | Butylene glycol | 5.0 | Butylene glycol | |
| | Water | TO100 | Water | |
| | SEPIMAX ZEN | 0.2 | Polyacrylate crosspolymer-6 | SEPPIC |
| | Carbopol ® Ultrez 21 | 0.1 | Acrylates/C10-30 alkly acrylate crosspolymer | Lubrizol |
| B | TEA | 0.1 | Triethanolamine | Guangzhou Chemical Reagent Factory |
| | MADECASSOSIDE | 0.2 | Madecassoside | SERDEX |
| | PONCIRUS EXTRACT (IT) | 1.0 | Water/glyceryl/PONCIRUS TRIFOLIATA fruit extract | SK BIOLAND |
| | IMMORTAL WA II | 5.0 | TREMELLA FUCIFORMIS extract/Dipropylene glycol/disodium EDTA/water | SK BIOLAND |
| | ULMUS EXTRACT PF | 1.0 | Water/Butylene glycol/Phenoxyethanol/ULMUS DAVIDIANA root extract | SK BIOLAND |
| | EUXYL K350 | 0.5 | Phenoxyethanol, methylparaben, ethylparaben, ethylhexylglyceryl | S&M |
| C | 86399137 | 0.008 | Flavor | DROM |
| | TAGAT CH40 | 0.024 | PEG-40 hydrogenated castor oil | EVONIK |

The preparation process of the hydrogel of Example 4 includes:

1. heating and stirring phase A to fully disperse evenly; and
2. after cooling, adding phase B and phase C in sequence, and stirring evenly.

The hydrogel of Example 4 is a light yellow transparent flowing gelatin, with pH=7.29, viscosity=5416 cps (5 #, 5 rpm), stable in heat resistance (48° C. for one month), and stable in cold resistance (−15° C. for one month).

The hydrogel of Example 4 can play a very good anti-allergic effect. The specific principle is as follows.

Main Active Ingredients:

IMMORTAL WA II: It is rich in active ingredients such as carotenoids, flavonoids and polysaccharides (iso-glucan, β-glucan and α-glucan), which can promote the expression of AQP-3 and hyaluronic acid synthase, and has the effects of moisturizing, anti-oxidation and promoting wound healing; in addition, the β-glucan contained therein also has the effects of improving skin immunity and anti-pollution.

Poncirus EXTRACT: It is extracted from the fruit of Fructus *Aurantii*, and contains more than 5000 ppm of poncirin. It has anti-allergic and anti-inflammatory effects. It is more effective when combined with *Portulaca oleracea* and can protect cells against UVB-induced cell death.

MADECASSOSIDE: It is extracted from wild *Centella asiatica* grown in Madagascar and rich in high-purity madecassoside, which can soothe the skin, rebuild extracellular matrix components, anti-inflammatory, regulate and protect the epidermis. In vivo experiments can relieve itching, anti-erythema and improve skin scaling, soothe sensitive skin, atopic dermatitis and psoriasis skin. It is suitable for care products for atopic dermatitis, sensitive and mature skin.

TABLE 5

Formulation of the hydrogel of Example 5

| | Raw material | Dosage % | INCI name | Supplier |
|---|---|---|---|---|
| A | Water | To100 | Water | |
| | LIPONIC BIO EG-1 | 3.0 | Glyceryl-26 | VANTAGE |
| | SEPIMAX ZEN | 0.2 | Polyacrylate crosspolymer-6 | SEPPIC |
| | Carbopol 941 | 0.2 | Acrylates/C10-30 alkly acrylate crosspolymer | Lubrizol |
| | Nicotinamide | 2.0 | Nicotinamide | MERCK |
| B | TEA | 0.2 | Triethanolamine | Guangzhou Chemical Reagent Factory |
| C1 | BIO-SODIUM HYALURONATE POWDER (MMW) | 0.03 | Sodium hyaluronate | SK BIOLAND |
| | MAGNOLIA EXTRACT | 1.0 | Water/butylene glycol/ MAGNOLIA SIEBOLDII extract | SK BIOLAND |
| C2 | SEPIWHITE MSH | 1.0 | Undecylenoyl phenylalanine | SEPPIC |
| | TEA | 0.5 | Triethanolamine | Guangzhou Chemical Reagent Factory |
| | Water | 20.0 | Water | |
| D | 1,3-Butylene glycol | 3.0 | 1,3-Butylene glycol | OXEA |
| | EUXYL K350 | 0.5 | Phenoxyethanol/ Methylparaben/ Ethylparaben/ Ethylhexylglyceryl | S&M |
| E | Flavor 86424047 | 0.06 | Flavor | DROM |
| | TAGAT CH40 | 0.18 | PEG-40 hydrogenated castor oil | EVONIK |

The preparation process of the hydrogel of Example 5 includes:
1. heating phase A to swell evenly, adding phase B and stirring to be clear and transparent;
2. pre-heating phase C2 and stirring to dissolve to be transparent, and adding phase C to A+B and stirring to disperse evenly; and
3. adding pre-dispersed phases D and E, and stirring evenly.

The hydrogel of Example 5 is a transparent flowing liquid, with pH=6.76, stable in heat resistance (48° C. for one month), and stable in cold resistance (−15° C. for one month).

The hydrogel of Example 5 can play a good role in whitening and removing spots. The specific principle is as follows.

Main Active Ingredients:
1. SEPIWHITE MSH: It is an antagonist of the melanocyte-stimulating hormone α-MSH in the process of melanin synthesis. It acts on multiple biochemical reaction stages of melanin formed by α-MSH, thereby comprehensively and effectively inhibiting the production of melanin, and the effect is more obvious and lasting. It can be used in various formulas to make skin clear.
2. BIO-SODIUM HYALURONATE POWDER (MMW): It is high-purity, high-quality sodium hyaluronate powder with a molecular weight of 1.3 to 1.8 megadaltons, which can form a viscoelastic, colorless, transparent and non-occlusive film on the skin, thereby having the effect of moisturizing and increasing skin elasticity.
3. *MAGNOLIA* EXTRACT: Because of its elegant appearance, it was once known as the "Heaven Flower" in Korea. It can inhibit the auto-oxidation of dopa, remove free radicals, and can inhibit the pigmentation caused by inflammation or UV irradiation, and has a significant improvement effect on chloasma.

TABLE 6

Formulation of the hydrogel of Example 6

| | Raw material | Dosage % | INCI name | Supplier |
|---|---|---|---|---|
| A | Water | TO100 | Water | |
| | Satiaxane VPC 930 | 0.18 | Xanthan gum | Cargill |
| | Liponic ™ BIO EG-1 | 3.00 | Glyceryl-26 | Vantage |
| | Carbopol 1 941 | 0.20 | Carbomer | Lubrizol |
| B | ALISTIN | 1.00 | Decarboxyl carnosine HCl/butylene glycol/ sodium methyl-paraben/water | EXSYMOL |
| | BPN-renovarin powder | 1.00 | Carnosine | United Laboratories |
| | Citric acid (20%) | 0.50 | Citric acid | Guangzhou Chemical Reagent Factory |
| C | SETILINE SN | 0.50 | TRIGONELLA FOENUM-GRAECUM seed extract | Greentech |
| | Water | 15.00 | Water | |
| D | euxyl K 350 | 0.50 | Phenoxyethanol/ Methylparaben/ Ethylparaben/ Ethylhexylglyceryl | S&M |
| | 1,3 butylene glycol | 3.00 | Butylene glycol | |
| | TAGAT CH40 | 0.15 | PEG-40 hydrogenated castor oil | EVONIK |
| | 86425579 | 0.04 | Flavor | Drom |

The preparation process of the hydrogel of Example 6 includes:
1. heating phase A and stirring evenly, and heating phase C to 80° C. to dissolve and then filtering with filter cloth; and
2. stirring to cool phase A to 45° C., adding phases B, C, and D (preservatives in D-phase are pre-dispersed evenly with butylene glycol, and FRAGRANCEs are pre-dispersed evenly with solubilizers), and stirring evenly.

The hydrogel of Example 6 is a light yellow transparent flowing gelatin.

The hydrogel of Example 6 can play a good role in anti-glycation and anti-free radicals. The specific principle is as follows.

Main Active Ingredients:
ALISTIN: It is a multi-effect anti-aging product, innovative in anti-aging and anti-oxidation. The accumulation of oxidation will cause the skin structure to collapse, lose its elasticity, and have wrinkles. ALISTIN not only removes free radicals, but also restores the peroxidized cell membranes, prevents the diffusion of oxidation reactions, and achieves oxidative repair, which neither VE nor VC can do. Glycation will cause protein cross-linking, wrinkles, dull and yellow skin. ALISTIN can not only prevent glycation, but also reverse protein glycation by competing with glycated protein. It is recommended for products for the treatment of aging skin or sun protection and post-sun repair, detoxification and resistance to pigmentation caused by aging. It is also a preferred raw material for improving efficacy in products such as whitening, anti-spot, and anti-hair loss.

SETILINE: It is small molecule galactomannan extracted from the outer skin of *Trigonella foenum-graecum* seeds using biotechnology, which can prevent the glycation of collagen and integrin in the dermis, promote the differentiation of epidermal keratinocytes, and increase the thickness of the epidermis, thereby having functions of anti-glycation, anti-aging, anti-wrinkle and improving skin barrier and suitable for anti-wrinkle, anti-aging, firming regeneration and moisturizing products.

BPN-renovarin powder: It is a powerful antioxidant and anti-protein glycation agent that can efficiently capture free radicals in the human body and inhibit the glycosylation and cross-linking reaction of skin proteins, slow down skin aging, and improve skin dullness.

TABLE 7

Formulation of the hydrogel of Example 7

| | Raw material | Dosage % | INCI name | Supplier |
|---|---|---|---|---|
| A | DEIONIZED WATER | TO100 | Water | |
| | Carbopol 941 | 0.18 | Carbomer | Lubrizol |
| | Satiaxane VPC930 | 0.08 | Xanthan gum | GARGILL |
| B | BPN-CIRUELO | 2.0 | Water/polysorbate-20/glyceryl/1,2-hexanediol/carbomer/palmitoyl tetrapeptide-7 | United Laboratories |
| | GLUCO-SYLRUTIN | 0.5 | Glucosylrutin | Nanjing Anyike |
| | TEA | 0.18 | Triethanolamine | Guangzhou Chemical Reagent Factory |
| | EDTA-2NA | 0.1 | EDTA-2NA | AKZO |
| | SOLIBERINE NAT | 0.5 | Water/Propylene Glycol/BUDDLEJA OFFICINALIS Extract | Greentech |
| | IMMORTAL WA II | 4.0 | TREMELLA FUCIFORMIS extract/dipropylene glycol/disodium EDTA/water | SK Bioland |
| C | EUXYL K350 | 0.5 | Phenoxyethanol/Methylparaben/Ethylparaben/Ethylhexylglyceryl | S&M |
| | Propylene Glycol | 8.0 | Propylene Glycol | |
| | Butylene glycol | 5.0 | Butylene glycol | OXEA |
| D | 86300185 | 0.1 | Flavor | Drom |
| | TAGAT CH40 | 0.3 | PEG-40 hydrogenated castor oil | Evonic |

The preparation process of the hydrogel of Example 7 includes:

dispersing phase A evenly, and then adding phases B, C and D and stirring evenly.

The hydrogel of Example 7 is a yellow liquid, with PH=5.83 (10% aqueous solution), viscosity=1485 cps (3 #20′), stable in heat resistance (48° C. for one month), and state in cold resistance (−15° C. for one month).

The hydrogel of Example 7 can play a very good anti-blue light effect, and the specific principle is as follows.

Main Active Ingredients:
1. BPN-CIRUELO: It can significantly reduce the level of inflammatory factors interleukin, thereby eliminating potential inflammation of the skin, restoring skin health, and reducing the damage of inflammation to the skin.
2. GLUCOSYLRUTIN: Glucosylrutin as a strong antioxidant, combined with the characteristics of UV absorption, can protect the epidermis and dermis from UV damage, so that the skin will no longer be troubled by such effects.
3. SOLIBERINE NAT: Derived from plateau plant *Buddleja officinalis*, it can resist strong sunlight radiation in plateau areas, and at the same time resist blue, infrared and ultraviolet light damage to the skin, inhibiting and repairing the occurrence of damage at various key points of light damage.

Effect Evaluation and Performance Testing

1. Moisture Retention Test (1) Test Description

Cumulative sample N=20 (sample amount to achieve T test)

Test object: to test the moisture retention of the hydrogel alone used in the two-dosage-form essence of Example 1 of the present application and the moisture retention of using different ratios of oil gel to verify that the oil gel can improve the moisture retention of the hydrogel.

Test method: 20 volunteers between the ages of 26-45 applied 0.04 μL of samples A, B, and C on the inside of one arm in a single application, and subjected to skin moisture content measurement with CK (Derma-Expert MC760) before applying and 1 h and 2 h after applying.

Testing Samples:
A: Hydrogel (Example 1)
B: Hydrogel (Example 1): Oil gel (Example 1)=4:1
C: Hydrogel (Example 1): Oil gel (Example 1)=1:1

(2) Test Environment

A blank control group is set up to test the influence of the external environment on the moisture retention test.

1 h VS blank; 2 h VS 1 h; 2 h VS blank.

(3) Test results (as shown in FIG. 15-20)
1. Samples A, B and C all have instant and long-lasting moisturizing effects;
2. Sample C has the best instant and long-lasting moisturizing effect;
3. The oil gel can effectively improve the moisture retention of the hydrogel; and
4. The combination of the hydrogel and the oil gel has good moisturizing effect.

The above embodiments are merely preferred embodiments of the present application, and shall not be used to limit the scope of protection of the present application. Any insubstantial changes and substitutions made by those skilled in the art on the basis of the present application belong to the scope of protection of the present application.

What is claimed is:

1. A two-dosage-form essence, comprising:
oil gel; and
hydrogel,
wherein the oil gel and the hydrogel are mixed according to a preset ratio during use,
wherein the oil gel comprises the following components in parts by weight:
0.1-6 parts of active ingredient;
15-35 parts of polyol;
0.1-1 part of sodium surfactin;
10-70 parts of oil; and
1-10 parts of water,
wherein the active ingredient comprises:
0.1-0.5 part of *Laminaria ochroleuca* extract complex;
0.1-0.5 part of algae extract complex;
2-5 parts of complex amino acid; and
0.1-1 part of eye circumference mixture,
wherein the polyol is one or any combination of glycerin, propylene glycol, 1,3-butylene glycol, sorbitol, and glycereth-26, and
wherein the oil is any combination of *Prunus amygdalus dulcis* oil, canola oil, C15-19 alkanes, *Simmondsia*

Chinensis seed oil, sunflower seed oil, soybean oil, squalane, octyldodecanol, mineral oil, dimethylsiloxane and cyclomethicone.

2. The two-dosage-form essence according to claim 1, wherein the oil gel comprises the following components in parts by weight:
 2-4 parts of active ingredient;
 20-30 parts of polyol;
 0.1-1 part of sodium surfactin;
 40-65 parts of oil;
 1-10 parts of water; and
 0.001-1 part of pigment.

3. The two-dosage-form essence according to claim 1, wherein the oil gel is prepared by a D-phase emulsification method.

4. The two-dosage-form essence according to claim 1, wherein the hydrogel comprises the following components in parts by weight: 70-90 parts of solvent, 1-15 parts of active component, 0.1-2 parts of thickener, 3-20 parts of humectant, 0-1 part of neutralizer, 0.1-1 part of preservative, 0.001-0.3 part of flavor, 0.01-1 part of solubilizer, 0-1 part of pH value regulator, and 0-0.5 part of chelating agent, wherein the active component is an anti-allergic active, a whitening active, an anti-glycation active or an anti-photoactive active.

5. The two-dosage-form essence according to claim 4, wherein the hydrogel comprises the following components in parts by weight: 70-90 parts of water, 3-8 parts of butylene glycol, 3-10 parts of refined peptide complex, 1-5 parts of phytosterols complex, 1-5 parts of glycereth-26, 0.1-1 part of polyacrylate crosspolymer-6, 0.1-0.5 part of xanthan gum, 0.1-1 part of preservative complex, 0.01-0.2 part of PEG-40 hydrogenated castor oil, and 0.01-0.2 part of flavor, wherein the refined peptide complex is a composition of water, polysorbate-20, carbomer, palmitoyl tetrapeptide-7, palmitoyl pentapeptide-4, acetyl hexapeptide-8, glycerol and 1,2-hexanediol; the phytosterols complex is a composition of water, propylene glycol and phytosterols; and the preservative complex is a combination of phenoxyethanol, methylparaben, ethylparaben and ethylhexylglyceryl.

* * * * *